United States Patent [19]

Waitzinger et al.

[11] Patent Number: 4,900,154

[45] Date of Patent: Feb. 13, 1990

[54] CONCRETE MIXER HAVING MEANS FOR DETERMINING THE CONSISTENCY OF CONCRETE MIXING THEREIN

[75] Inventors: Franz Waitzinger, Nersingen; Gerhard Hudelmaier, Ulm/Donau, both of Fed. Rep. of Germany

[73] Assignee: Ingrid Hudelmaier, Fed. Rep. of Germany

[21] Appl. No.: 246,868

[22] Filed: Sep. 20, 1988

[30] Foreign Application Priority Data

Sep. 24, 1987 [DE] Fed. Rep. of Germany ....... 3732231

[51] Int. Cl.$^4$ .......................... B28C 5/32; B28C 7/12; G01N 11/10; G01N 11/16
[52] U.S. Cl. ............................. 366/56; 73/54; 73/59; 366/40; 366/64
[58] Field of Search .................... 366/1, 2, 27, 30, 40, 366/42, 44, 53, 54, 56, 57, 58, 59, 60, 61, 64, 117, 118, 124, 128, 142, 600, 34, 17, 151, 152, 65, 66, 67, 160; 73/54, 59, 570, 862.37, 862.19

[56] References Cited

U.S. PATENT DOCUMENTS

| | | | |
|---|---|---|---|
| 1,730,893 | 10/1929 | Lichtenberg | 73/59 X |
| 2,089,604 | 8/1937 | Hagy | 366/56 X |
| 2,409,014 | 10/1946 | Bohmer et al. | 73/54 |
| 2,630,706 | 3/1953 | Maxon, Jr. | 73/54 |
| 2,643,542 | 6/1953 | Cronk | 73/54 |
| 3,933,341 | 1/1976 | Hudelmaier | 366/57 |
| 4,027,859 | 6/1977 | Stone | 366/151 X |
| 4,356,723 | 11/1982 | Fay | 73/54 |
| 4,436,429 | 3/1984 | Strong et al. | 366/142 X |
| 4,490,045 | 12/1984 | Hudelmaier | 366/56 |
| 4,522,499 | 6/1985 | Hudelmaier | 366/56 |
| 4,544,275 | 10/1985 | Hudelmaier | 366/151 X |
| 4,585,355 | 4/1986 | Waitzinger | 366/56 X |
| 4,704,898 | 11/1987 | Thone | 73/54 |
| 4,730,934 | 3/1988 | Schwing | 366/40 |

FOREIGN PATENT DOCUMENTS

| | | | |
|---|---|---|---|
| 2429858 | 1/1976 | Fed. Rep. of Germany | 366/17 |
| 3026033 | 1/1982 | Fed. Rep. of Germany | 366/54 |
| 159123 | 11/1963 | U.S.S.R. | 366/56 |
| 903129 | 2/1982 | U.S.S.R. | 366/56 |
| 961983 | 9/1982 | U.S.S.R. | 366/64 |

Primary Examiner—Harvey C. Hornsby
Assistant Examiner—Scott J. Haugland
Attorney, Agent, or Firm—James E. Nilles; Donald C. McGaughey

[57] ABSTRACT

A concrete mixer is disclosed having a mixing drum and a drag body is mounted in the drum which has a drag surface positioned to at least partially come into contact with concrete in the drum during a measuring phase in the concrete mixing operation. A hydraulic driving circuit is provided to oscillate the drag body at least during the measuring phase. A pressure sensor is connected in the hydraulic driving circuit for measuring the actual pressure value in the hydraulic driving circuit which is indicative of the flow resistance on the drag surface during the measuring phase of the mixing operation.

3 Claims, 4 Drawing Sheets

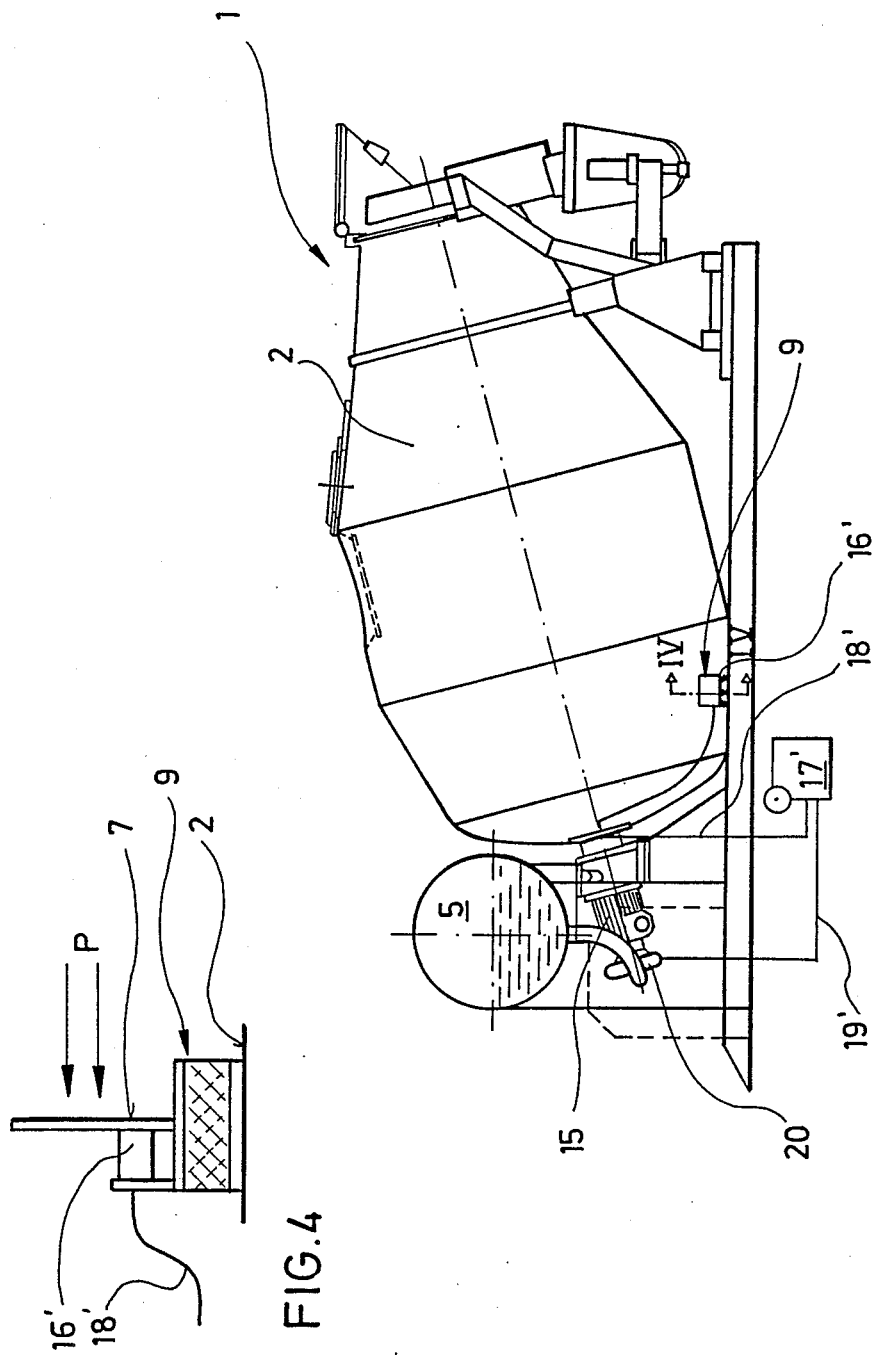

CONCRETE MIXER HAVING MEANS FOR DETERMINING THE CONSISTENCY OF CONCRETE MIXING THEREIN

The invention relates to a method for determining the consistency of concrete in a kinetic mixer by measuring a kinetic resistance, and to a concrete mixer for performing the method, comprising a mixing drum and means for determining the consistency of the concrete including a drag surface disposed within the drum so as to at least partially come into contact with the concrete during the measuring phase.

BACKGROUND OF THE INVENTION

A method and a concrete mixer of this type are known from practical applications. The consistency is determined by measuring the driving power absorbed by the mixing drum. This is carried out by measuring the driving torque or the hydraulic pressure of a hydraulic motor driving the mixing drum. The drag surface opposing the flow of the concrete and substantially determining the driving torque absorbed by the mixing drum is formed by the interior wall surface of the mixing drum and by installations within the mixing drum, such as mixer blades and the like. During the phase in the course of which the driving power absorbed by the mixing drum is measured, these drag surfaces are only intermittently and/or partially in contact with the concrete. The size of the drag surface is largely dependent on the filling degree of the mixing drum. In addition, the driving torque absorbed by the mixing drum largely depends on whether or not the concrete mixer stands on level ground. Particularly in the case of mobile mixers it is not always possible to ensure that they always stand on level ground at a construction site. Since the consistency of the concrete is adjusted on the base of a comparison of the measured driving torque to a predetermined reference torque, the numerous distorting influences prevent an accurate adjustment of the consistency from being reliably achieved by the known method and with the known concrete mixer, so that the adjustment of the consistency is rather arrived at by chance.

SUMMARY OF THE INVENTION

It is therefore an object of the invention to provide a concrete mixer for performing the method so as to permit the consistency of the concrete to be more accurately determined and to thus be more reliably adjusted.

With regard to the method this object is attained according to the invention by measuring the flow resistance of a drag body immersed in the concrete during the measuring phase and moving relative to the concrete. This results in the advantage that the drag surface of the drag body exposed to the concrete remains constant during the full duration of the measuring phase. This drag surface is independent of the filling degree of the concrete mixer and also independent of whether the concrete mixer stands on level or sloping ground. The consistency of the concrete to be prepared in the concrete mixer may thus be determined substantially independent of any exterior influences.

Disclosed in DE-OS No. 31 13 785 is an apparatus for determining the consistency of ready-mixed concrete. This apparatus operates with a measuring agitator for generating a concrete flow directed on a measuring element the deformation of which is measured for determining the consistency of the concrete. This apparatus is rather complicated, requiring as it does a measuring agitator with its own driving mechanism in addition to the measuring element proper. In contrast thereto, the method according to the invention makes use of the movement of the concrete brought about in any case by the rotation of the drum or any other mixing mechanism for determining the consistency of the concrete.

According to a particularly preferred embodiment of the method, one measures the flow resistance created by an oscillating movement of the drag body in the concrete. In this manner the drag body is no longer or not only passively exposed to the flow of the concrete, but performs an active movement on its own. In this manner the measurement of the flow resistance, which of course depends on the viscosity and thus on the consistency of the concrete, is substantially only influenced by the type of the oscillating movement of the drag body. The oscillating movement of the drag body may of course be effectively controlled by controlling the power input to the oscillating mechanism of the drag body.

The measured flow resistance is advantageously compared to a predetermined flow resistance corresponding to a desired consistency, and adjusted to substantially match this predetermined flow resistance by adding liquid to the concrete. In this manner it is possible to reliably adjust the concrete to the desired consistency.

According to a particularly advantageous aspect, the consistency of the concrete is adjusted by incrementally adding a liquid and, subsequent to an addition of liquid, mixing the concrete until the measured flow resistance assumes a substantially constant value, before any further liquid is added. In this manner it may be ensured that the concrete has been properly mixed throughout before it is adjusted to a more liquid consistency by a further addition of liquid.

Since the consistency of the concrete and thus also the flow resistance to be measured do not necessarily vary in linear relationship with the mixing time, the time required for properly mixing the concrete may in an advantageous manner be shortened by continually measuring alterations of the measured flow resistance after an addition of liquid and mixing the concrete until the measured value of said alteration is smaller than a preselected reference value before any further liquid is added. This manner of carrying out the method according to the invention results in an acceleration of the concrete mixing operation particularly at the beginning, when the measured flow resistance is still far above the predetermined flow resistance.

With regard to the concrete mixer, the stated object is attained according to the invention by the provision that the drag surface is formed on a drag body completely immersed in the concrete at least during the measuring phase. A concrete mixer of this construction permits the method according to the invention to be performed in a particularly simple manner.

In the case of a concrete mixer having a rotatable mixing drum, a particularly simple solution may be achieved by the provision that the drag body is fixedly mounted on an interior wall surface of the mixing drum. This manner of mounting the drag body permits static measurements of the consistency of the concrete to be taken. The rotation of the mixing drum causes the concrete to flow past the drag body, so that a mechanism for moving the drag body is not required. This manner of mounting the drag body also permits existing concrete mixers to be equipped therewith in a particularly simple manner.

In the case of concrete mixers provided with an oscillating body, the drag body may advantageously be formed by the oscillating body itself. Oscillating bodies of this type are described for instance in German Pat. No. 3,201,162. The advantage obtained by using such oscillating bodies as drag bodies particularly results from the fact that the flow about the oscillating body is substantially created by the osciallation of the body itself and is thus substantially independent of exterior influences. The influence of the drum rotation may be neglected in most cases when the oscillating body is located substantially at the center of the mixing drum.

In the case of a hydraulically operated oscillating body the flow resistance may be measured in a particularly simple manner by providing a pressure sensor in the hydraulic driving circuit. In this case the flow resistance is thus, indirectly measured by way of the power absorption of the hydraulic drive mechanism of the oscillating body.

The consistency of the concrete may be adjusted in a particularly simple and reliable manner when the means for determining the consistency of the concrete includes a control unit operable to compare the values measured by the pressure sensor to predetermined reference values. The control unit may be designed to compare the predetermined reference value to a mean value or a variation coefficient. The measurement may also be performed by way of an integral evaluation. The measurements may be performed after a predetermined time during the mixing process, after a predetermined number of drum revolutions, or in a predetermined position of the drum. The state of the control means is advantageously verified before starting operations, and considered as a correction factor for the measurements.

The control unit is advantageously operable to generate a control signal in response to the value measured by the pressure sensor remaining substantially constant for a predetermined interval, or to the alteration of the pressure values dropping below a predetermined rate. The control signal thus generated may be used for actuating a liquid valve, so that further water is added when the value previously measured by the pressure sensor is still above the predetermined pressure value.

In a particularly advantageous embodiment the control unit is operable to generate a switch-off signal in response to the value measured by the pressure sensor substantially corresponding to the predetermined pressure value for a predetermined interval. This switch-off signal indicates that the concrete now has the desired consistency. This control unit thus permits the consistency of the concrete to be readily and automatically adjusted to the desired value.

DESCRIPTION OF THE DRAWINGS

The invention shall now be described in detail with reference to the accompanying drawings, wherein:

FIG. 3 shows a view similar to FIG. 2 of a concrete mixer according to a second embodiment of the invention, FIG. 4 shows a detail of FIG. 3 in a sectional view taken along the line IV—IV.

DESCRIPTION OF THE PREFERRED EMBODIMENTS

Figure 1:
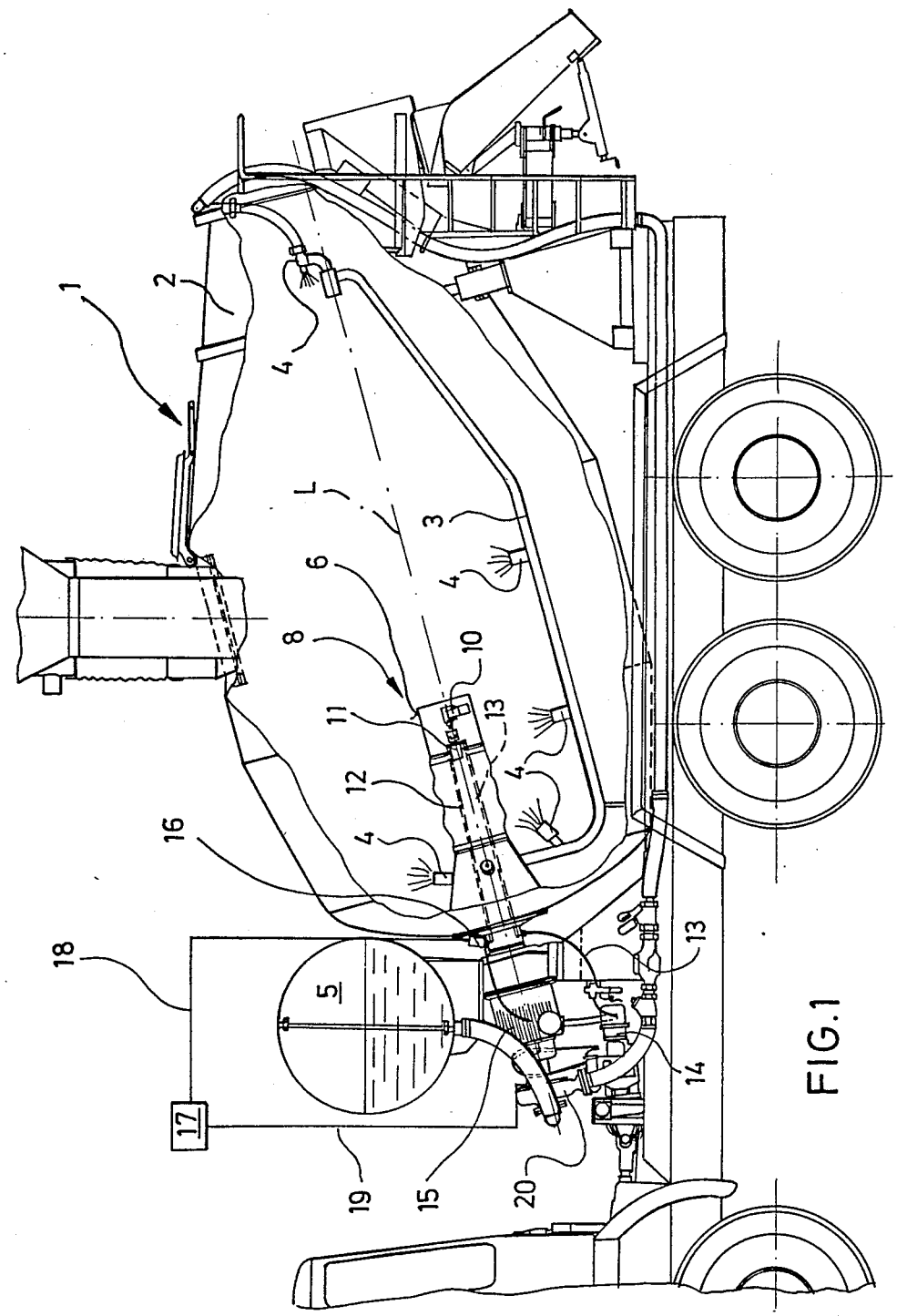
FIG. 1 shows a partially sectioned sideview of a concrete mixer according to a first embodiment of the invention.
Figure 2:
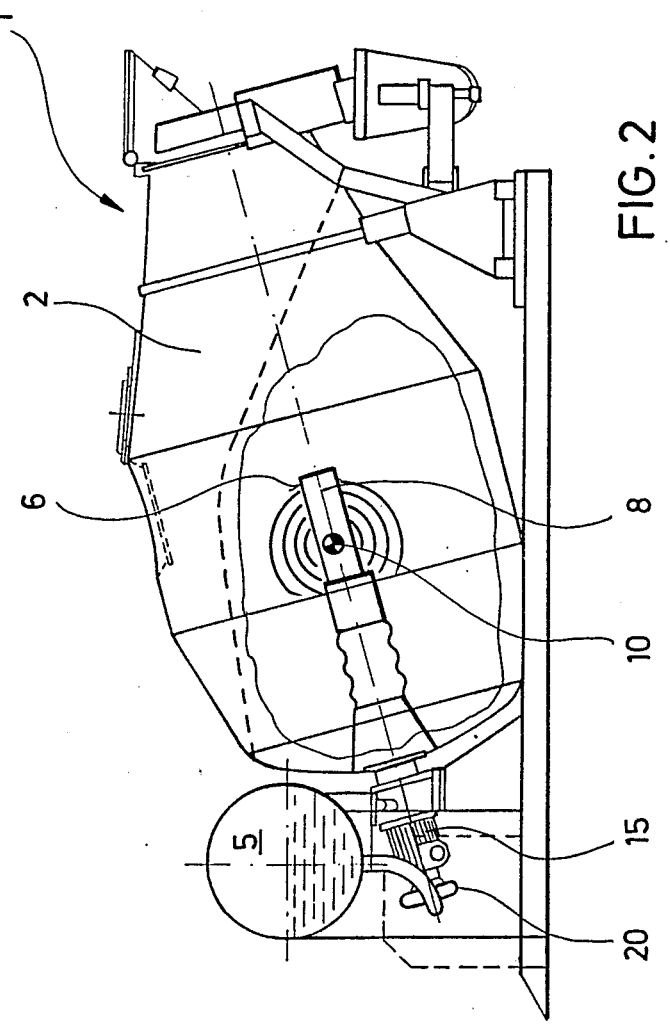
FIG. 2 shows a diagrammatical sideview of the concrete mixer of FIG. 1 in the filled state.

Shown in FIGS. 1 to 3 are partially sectioned sideview of a concrete mixer 1, specifically a so-called concrete mixer truck. Concrete mixer 1 is mounted on the wheeled frame of a truck and comprises a rotatable mixing drum 2 and an interiorly mounted water feed pipe 3 provided with outlet nozzles 4 for supplying water from a water tank 5 to the interior of mixing drum 2.

Concrete mixer 1 further comprises means for determining the consistency of the concrete to be mixed in mixing drum 2. In all embodiment of the invention, the means for determining the consistency of the concrete comprises a drag surface 6 or 7, respectively, coming into contact with the concrete at least during a measuring phase. Drag surfaces 6 or 7, respectively, are formed on a drag body 8 or 9, respectively, so that they are completely immersed in the concrete during the measuring phase.

In the first embodiment shown by way of example in FIGS. 1 and 2, drag body 8 is formed as an oscillating body. An oscillating body of this type has already been described in German Pat. No. 3,201,162. The oscillating body 8 employed in the present embodiment is particularly well recognizable in the cross-sectional view of FIG. 1. It is formed in the shape of a cylinder disposed on the longitudinal center axis of mixing drum 2. Mounted within the cylinder of oscillation body 8 is a vibration generator in the form of an excentrically and rotatably mounted flyweight.

A shaft of the vibration generator—not identified by a specific reference numeral—is coupled to a hydraulically operated gear motor 11. Hydraulic pipes 12 and 13 extend from gear motor 11 through the front end of mixing drum 2 to a hydraulic pump 14. A hydraulic drive mechanism 15 for mixing drum 2 interposed between hydraulic pump 14 and gear motor 11 is of conventional construction and therefore not described in detail.

Connected to at least one of hydraulic pipes 12 and 13, respectively, is a pressure sensor 16 connected to a control unit 17 via a control cable 18. A further control cable 19 connects control unit 17 to a feeder pump 20 operable to feed water from water tank 5 to the interior of drum 2. As an alternative, control unit 17 may also be connected to a stop valve (not shown) provided in water feed pipe 3.

Control unit 17 is designed to compare the values measured by pressure sensor 16 to a predetermined reference value. This reference value may be selected within the purview of a program additionally considering certain influences determining the consistency, such as the composition of the concrete, condition of the filler materials and the cement and the like.

Figure 5:
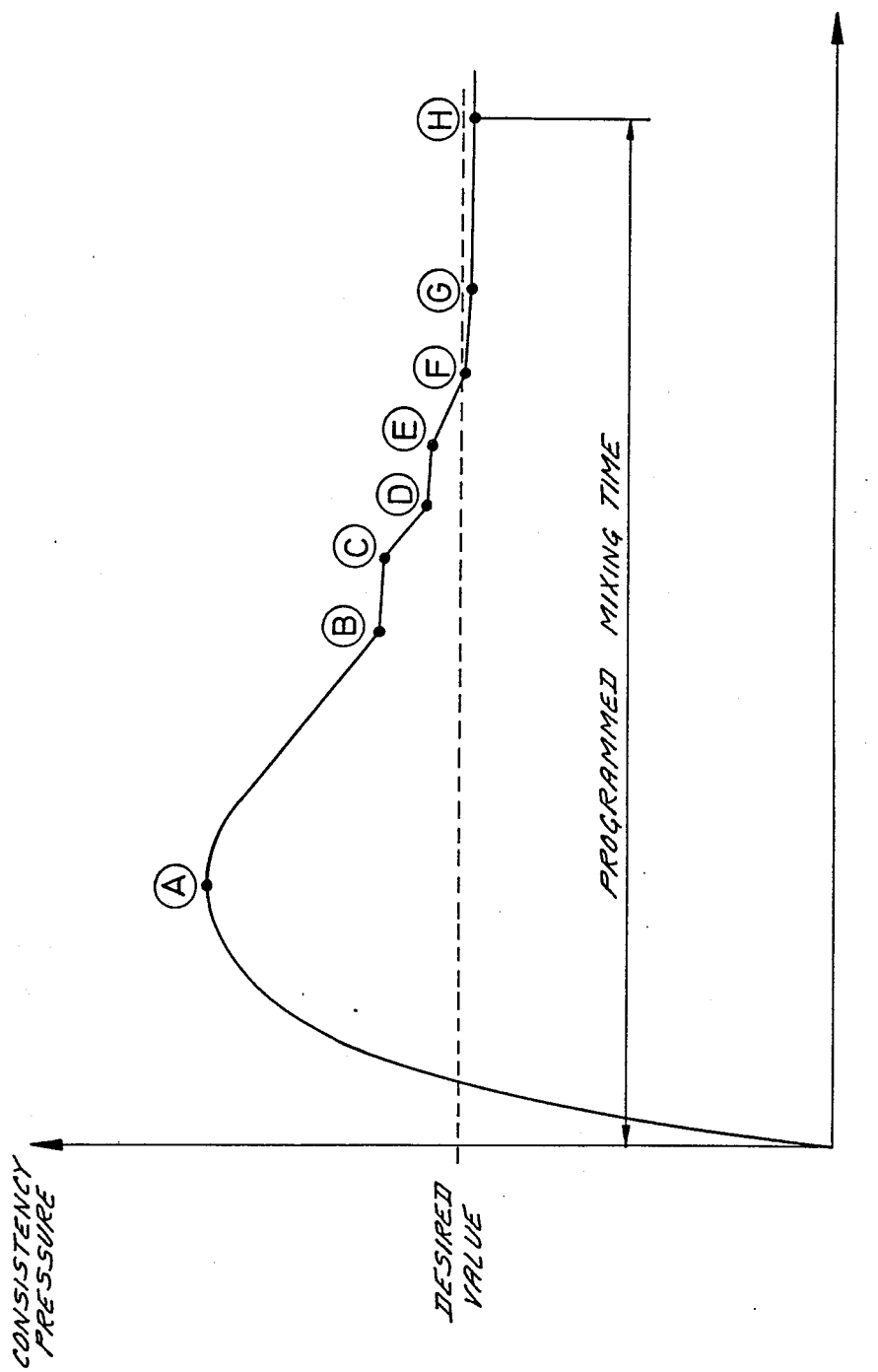
FIG. 5 shows a diagram illustrating the control operations for adjusting the consistency of the concrete in the concrete mixer.

The method according to the invention shall now be explained in detail with reference to the concrete mixer truck shown by way of example in FIGS. 1 and 2, and to the operating program depicted in FIG. 5.

After mixing drum 2 has been filled, it is rotated about its longitudinal axis L by rotary drive mechanism 15. To this purpose hydraulic pump 14 is operated to supply drive mechanism 15 with a pressurized fluid via the associated hydraulic pipes. At the same time, gear motor 11 of vibration generator 10 is supplied with the pressurized fluid from pump 14 via hydraulic pipes 12 and 13, so that oscillating body 8 is caused to perform excentric oscillations. This results in the circumferential surface 6 of oscillating body 8, which is completely immersed in the concrete mixture, to perform an oscillating movement relative to the concrete mixture. The concrete contained in mixing drum 2 exerts a resistance to the movement of circumferential surface 6 of oscillating body 8, this resistance being dependent on the consistancy of the concrete. The oscillation of oscillating body 8 is opposed by a strong resistance as long as the concrete mixture is relatively dry. The oscillation results in compaction of the concrete mixture, so that the pressure in hydraulic pipes 12 and 13 as measured by pressure sensor 16 rises to a maximum pressure value A within a relatively short time. Even while the pressure thus rises, control unit 17 operates to activate liquid pump 20 or to open a valve (not shown) provided in feed pipe 3, so that water is supplied from water tank 5 to the concrete mixture via feeder pipe 3 and outlet nozzles 4. After the pressure measured by pressure sensor 16 and corresponding to the power absorbed by oscillation body 8 has reached its maximum value, the continued addition of water results in a softening of the concrete mixture, so that the pressure measured by pressure sensor 16 drops below the maximum value A. At a point above the predetermined reference pressure value corresponding to the desired consistency of the concrete the addition of water is stopped (point B). The minimum amount of water required in any case has now been completely supplied to mixing drum 2. The oscillating body, or the vibration generator 10 mounted therein, respectively, continues to be operated until the pressure measured by pressure sensor 16 has remained substantially constant for a determined interval (B-C). As shown in the control diagram, the measured pressure varies very little during the interval B-C, which is indicative of an effective mixing action by oscillating body 8.

At point c the pressure measured by pressure sensor 16 is still noticeably higher than the reference value, so that further water is added. This additional amount of water is considerably smaller than the minimum amount of water already supplied previously. At another point D, again above the reference value, the addition of water is stopped, whereupon the pressure measured by pressure sensor 16 will again noticeably decrease. The measured pressure then remains nearly constant up to point E, but is still somewhat higher than the reference value. At point E still further water is therefore added, the amount thus added being again smaller than that added in the previous step. As soon as the pressure measured by pressure sensor 16 corresponds to the pressure reference value as at point F, the addition of water is definitely stopped. At point G the measured pressure has reached a constant value, whereupon oscillating body 8 continues to be operated until reaching point H for still further improving the homogeneization of the concrete. At point H the concrete in mixing drum 2 thus has the desired consistency.

During all of this control program, the oscillating body is completely immersed in the concrete so that the active drag surface 6 exposed to the concrete, i.e. the circumferential surface of oscillating body 8, is not subjected to any alterations during the measuring phase. This permits the consistency of the concrete to be accurately adjusted substantially independent of exterior influences, it being of no importance particularly whether the charge in mixing drum 2 is somewhat greater or smaller or whether mixer truck 1 stands on uneven ground.

FIGS. 3 and 4 show another embodiment of the concrete mixer according to the invention, the operation of which substantially corresponds to that of the embodiment described above.

Identical or similar components have therefore been designated by the same reference numerals; the description shall be restricted to differences from the embodiment described above.

By way of difference from the first embodiment, drag surface 7 is provided on a drag body 9 fixedly mounted on an interior wall surface of mixing drum 2 so as to be rotated in unison therewith. As shown in FIG. 4, the concrete contained in mixing drum 2 flows about drag surface 7 in the direction of arrow P, drag surface 7 being formed as a baffle plate of a predetermined size. In this manner, baffle plate 7 is subjected to pressure acting thereon from the right in FIG. 4.

Disposed at the rear face of baffle plate 7 is a pressure sensor 16' connected to a control unit 17' by a control cable 18'. Liquid feed pump 20 of the concrete mixer is connected to control unit 17' via control cable 19'. Pressure sensor 16' may for instance be a piezoelectric sensor element.

As mixing drum 2 is rotated about its longitudinal center axis L, baffle plate 7 of drag body 9 is subjected to pressure acting thereon in the direction of arrows P, resulting in a certain flow resistance opposing the flow of the concrete. The level of the pressure measured by pressure sensor 16' is indicative of the flow resistance and thus of the viscosity, eg. the consistency of the concrete. As a result of the rotation of baffle plate 7 of drag body 9 in unison with mixing drum 2 it may happen, depending on the location of drag body 9 on the interior wall surface of mixing drum 2, that drag body 9 is alternately immersed into and raised from the concrete. As a result, pressure sensor 16' may register a sudden pressure drop and a sudden pressure rise during each revolution of mixing drum 2. The sudden pressure rise and the sudden pressure drop indicate the beginning and the end of a respective measuring phase during which drag surface 7 of drag body 9 is completely immersed in the concrete. This may be taken into account in the design of control unit 17', so that the concrete may be adjusted to the desired consistency substantially regardless of the filling degree of mixing drum 2.

Apart from the fact that in the second embodiment the revolution the method for adjusting the consistency of the concrete is no different from that of the first embodiment. The control unit 17' has an operating cycle substantially similar to the control operation depicted in FIG. 5.

The drag surface may also be mounted at a fixed position relative to the wheeled frame of mixer truck 1, so that it does not rotate in unison with the mixing drum, and so that it is immersed in the concrete during the full revolution of the drum.

For eliminating the influences of pressure variations caused by inclusions of dry matter, the control unit may be designed to generate control signals only in response to mean pressure values, variation coefficients, or an integrating evaluation.

In the embodiments shown herein, the pressure measurements are preferably taken at a constant rotational speed of the drum or at a constant oscillation frequency of the oscillating body, respectively. When the drag surface is disposed on the vibrating body, however, as in the first embodiment, the influence exerted by the rotational speed of the drum on the flow resistance exerted by the drag surface plays only an insignificant role and may therefore be left out of account, depending on the construction of the oscillating body.

I claim:

1. A concrete mixer for determining the consistency of concrete mixed therein during a measuring phase in a concrete mixing operation comprising: a mixing drum (2); a drag body (8, 9) mounted in said drum to be completely immersed in the concrete at least during the measuring phase and having a drag surface (6, 7) positioned to at least partially come into contact with concrete in said drum during said measuring phase; a hydraulic driving circuit (11–14) operatively connected to oscillate said drag body; and a pressure sensor (16, 16') connected to said hydraulic driving circuit for measuring the actual pressure value in said hydraulic driving circuit indicative of flow resistance on said drag surface during said measuring phase.

2. A concrete mixer according to claim 1 wherein said mixer includes a control unit (17, 17') having a predetermined pressure value; and means for receiving said actual pressure value, comparing said actual pressure value with said predetermined pressure value and generating a control signal in response to said actual pressure value remaining substantially constant for a predetermined time interval (B-C, D-E).

3. A concrete mixer according to claim 2 wherein said control unit (17, 17') has means for generating a switch-off signal in response to the actual pressure value measured by said pressure sensor substantially corresponding to said predetermined pressure value for a predetermined time interval (G-H).

* * * * *